United States Patent [19]
Kudo et al.

[11] Patent Number: 5,869,268
[45] Date of Patent: Feb. 9, 1999

[54] METHODS FOR PRODUCING HUMAN LYMPHOCYTES AND HUMAN MONOCLONAL ANTIBODIES, AND HUMAN MONOCLONAL ANTIBODIES PRODUCED THEREBY

[75] Inventors: Toshio Kudo, Sendai; Shuichi Hiyamuta, Sodegaura; Toshiyuki Tanedani, Sodegaura; Akihiko Kadota, Sodegaura, all of Japan

[73] Assignee: Idemitsu Kosan Company Limited, Tokyo, Japan

[21] Appl. No.: 815,953

[22] Filed: Mar. 13, 1997

Related U.S. Application Data

[62] Division of Ser. No. 969,336, Oct. 30, 1992, Pat. No. 5,681,729.

[30] Foreign Application Priority Data

| Oct. 30, 1991 | [JP] | Japan | 3-311665 |
| Feb. 20, 1992 | [JP] | Japan | 4-70187 |
| Aug. 20, 1992 | [JP] | Japan | 4-244250 |

[51] Int. Cl.$^6$ .......................... G01N 33/574; C07K 16/18
[52] U.S. Cl. ................ 435/7.23; 435/391.3; 530/388.15; 530/388.8; 530/391.3; 530/391.7; 436/64
[58] Field of Search ............................ 530/388.15, 388.8, 530/391.7; 436/63, 64, 813; 435/7.23, 391.3

[56] References Cited

U.S. PATENT DOCUMENTS 5,411,881  5/1995  Matsuda et al. .................... 435/240.27

FOREIGN PATENT DOCUMENTS

| 322240A2 | 6/1989 | European Pat. Off. . |
| 438053A1 | 7/1991 | European Pat. Off. . |
| 57-080327 | 5/1982 | Japan . |
| 1202295 | 8/1989 | Japan . |
| 1216267 | 8/1989 | Japan . |
| 3240498 | 10/1991 | Japan . |
| 9116910 | 11/1991 | WIPO . |
| 9118615 | 12/1991 | WIPO . |
| 9305796 | 4/1993 | WIPO . |

OTHER PUBLICATIONS

Borrebaeck, C., "Strategy for the Production of Human Monoclonal Antibodies Using In Vitro Activated B Cells," *J. Immunol. Methods*, vol. 123, pp. 157–165 (1989).

Usuba, O., "Establishment of a Human Monoclonal Antibody to HD Antigen as a Tumor–Associated Carbohydrate Antigen." *Jpn. J. Cancer Res.*, vol.79, No.12, pp. 1340–1348 (1988) (Abstract only).

Gathury, J., "In Vitro Immunization of Tumor–Associated Glycolipid Antigens for Human Monoclonal Antibody Preparation," *Proc. Annu. Meet Jpn. Cancer Assoc.*, vol.49, p. 353 (1990) (Abstract only).

Carlsson, R., "Human PBL Transplanted into SCID Mice Constitute an In Vivo Culture System Exhibiting Several Parameters Found in a Normal . . . ," *J. Immunol.*, vol.148, No.4, pp. 1065–1071 (1992).

Duchosal, M., "Immunization of hu–PBL–SCID Mice and the Rescue of . . . ," *Nature*, vol.355, pp. 258–262 (1992).

Saxon, A., "Limited B Cell Repertoire in SCID Mice Engrafted with PBMC from Immunodeficient or Normal Humans," *J. Clin. Invest.*, vol.87, pp. 658–665 (1991).

Mosier, D.C., "Transfer of a Functional Human Immune System to Mice with Severe Combined Immunodeficiency," *Nature*, vol.335, pp. 256–259 (1988).

Mazingue, C., "Obtention of a Human Primary Humoral Response Against Schistosome . . . ," *Eur. J. Immunol.*, vol.21, pp. 1763–1766 (1991).

Mukuria et al. (1986) *J. Biochem* 100(2):469–475, Abstract.

Kudo et al. (1992) *Kohoku J. Exp. Med.* 168(2)323–327.

Markham et al. (1992) *Infection and Immunity* 60:(6):2305–2308.

*Primary Examiner*—Toni R. Scheiner
*Attorney, Agent, or Firm*—Birch, Stewart, Kolasch & Birch, LLP

[57] ABSTRACT

A method for producing a human lymphocyte producing an antibody specific to a desired antigen, a method for producing a monoclonal antibody, as well as monoclonal antibodies produced by the method, are described. The present invention provides a method for producing a human lymphocyte producing an antibody comprising, in the order mentioned, the steps of: transplanting human lymphocytes into an immunodeficient animal so that the human lymphocytes take in the animal body; immunizing the animal with a desired antigen so as to generate human lymphocytes producing an antibody specific to the antigen; and recovering the human lymphocytes producing the antibody from the animal. The present invention also provides a method for producing a monoclonal antibody comprising, in the order mentioned, the steps of: immortalizing the human lymphocytes producing the antibody which were obtained by the above-mentioned method of the present invention; cloning the obtained immortalized human-derived lymphocytes producing the antibody; and recovering a monoclonal antibody specific to the desired antigen from the cloned immortalized human-derived lymphocytes.

10 Claims, 7 Drawing Sheets

GM1  GM2  GM3  HD3

Colored by Orcinol Sulfate

GM1  GM2  GM3  HD3

Stained with Antibody

METHODS FOR PRODUCING HUMAN LYMPHOCYTES AND HUMAN MONOCLONAL ANTIBODIES, AND HUMAN MONOCLONAL ANTIBODIES PRODUCED THEREBY

This application is a divisional of copending application Ser. No. 07/969,336, filed on Oct. 30, 1992, now U.S. Pat. No. 5,681,729, the entire contents of which are hereby incorporated by reference.

BACKGROUND OF THE INVENTION

I. Field of the Invention

The present invention relates to a method for producing human lymphocytes producing antibodies specific to desired antigens and a method for producing monoclonal antibodies, as well as to monoclonal antibodies produced thereby.

II. Description of the Related Art

Antibodies are conventionally administered to humans for the purpose of treating or diagnosing various diseases. The conventionally used antibodies are prepared mainly from animals such as mice. However, when an antibody obtained from an animal is administered to a human for treating a disease, an anti-antibody is produced, so that the half life of the administered antibody is short and sufficient effect is not obtained by repeatedly administering the antibody. Further, there are antigens such as HD antigen which cannot be prepared from mice. Although this problem may be overcome by directly recovering lymphocytes from humans, since the human lymphocytes producing an antibody specific to the desired antigen cannot be recovered systematically, this approach is not industrially viable. Further, since it is not generally permitted to immunize human with a desired antigen from an ethical view point, it is difficult to obtain a lymphocyte producing the desired antibody. Further, even in cases where the desired antigen can be administered to humans, it is impossible to repeatedly immunize the human for a long time, so that it is difficult to induce a sufficient immune response.

To overcome the above-mentioned problem, the transformation method employing Epstein-Barr virus (D. Kozbor et al., Methods in Enzymology, 121 140 (1986)) and the in vitro sensitization method (C. A. K. Borrebaeck et al., J. of Immunology, 136, 3710 (1986)) have been proposed. However, most of the antibodies produced by these methods are IgMs. IgMs are difficult to purify and their stabilities are not high. Further, with the in vitro sensitization method, since lymphocytes are cultured with an antigen, the time period in which the lymphocytes can be sensitized is short, so that it is difficult to induce sufficient antibody production. Thus, a method for producing a human monoclonal antibody, especially a human IgG antibody, which is specific to a desired antigen, is desired.

SUMMARY OF THE INVENTION

Accordingly, an object of the present invention is to provide a method for producing a human lymphocyte which produces an antibody, especially IgG antibody, which is specific to a desired antigen. Another object of the present invention is to provide a method for producing human monoclonal antibodies using the lymphocyte produced by the method of the present invention. Still another object of the present invention is to provide human monoclonal antibodies useful for treatment or diagnosis of cancers.

The present inventors intensively studied to find that human lymphocytes which mainly produce IgG and IgA antibodies can be obtained by transplanting human lymphocytes to an immunodeficient animal so that the human lymphocytes take in the animal body; and immunizing the animal with a desired antigen so as to generate human lymphocytes producing an antibody specific to the antigen, thereby completing the present invention.

That is, the present invention provides a method for producing a human lymphocyte producing an antibody comprising, in the order mentioned, the steps of: transplanting human lymphocytes to an immunodeficient animal so that the human lymphocytes take in the animal body; immunizing the animal with a desired antigen so as to generate human lymphocytes producing an antibody specific to the antigen; and recovering the human lymphocytes producing the antibody from the animal.

The present invention also provides a method for producing a monoclonal antibody comprising, in the order mentioned, the steps of: immortalizing the human lymphocytes producing the antibody, which were obtained by the above-mentioned method of the present invention; cloning the obtained immortalized human-originated lymphocytes producing the antibody; and recovering a monoclonal antibody specific to the desired antigen from the cloned immortalized human-originated lymphocytes.

The present invention still further provides a human monoclonal antibody which specifically reacts with the extracellular domain of human c-erbB2 cancer gene product.

The present invention still further provides an anti-HD human monoclonal IgG antibody which specifically reacts with HD antigen.

By the present invention, a method for producing human lymphocytes which produce the desired antibodies, as well as a method for producing a human monoclonal antibody using the human lymphocytes is provided. In the method of the present invention, since animals are immunized, antibodies specific to the desired antigen can be produced industrially irrespective of the type of the antigen. Further, since the time period for immunization can be made long, sufficient induction of antibody production can be attained. Further, the antibodies produced by the method of the present inventions are mainly IgG and IgA, so that the antibodies may be purified easily and their stabilities are high. Still further, by the present invention, a human monoclonal antibody specific to the extracellular domain of the human c-erbB2 gene product is provided. This monoclonal antibody is useful for the diagnosis and treatment of cancers. Still further, by the present invention, an anti-HD human monoclonal antibody is also provided, which is also useful for the diagnosis and treatment of cancers.

DETAILED DESCRIPTION OF THE PREFERRED EMBODIMENTS

Figure 1:
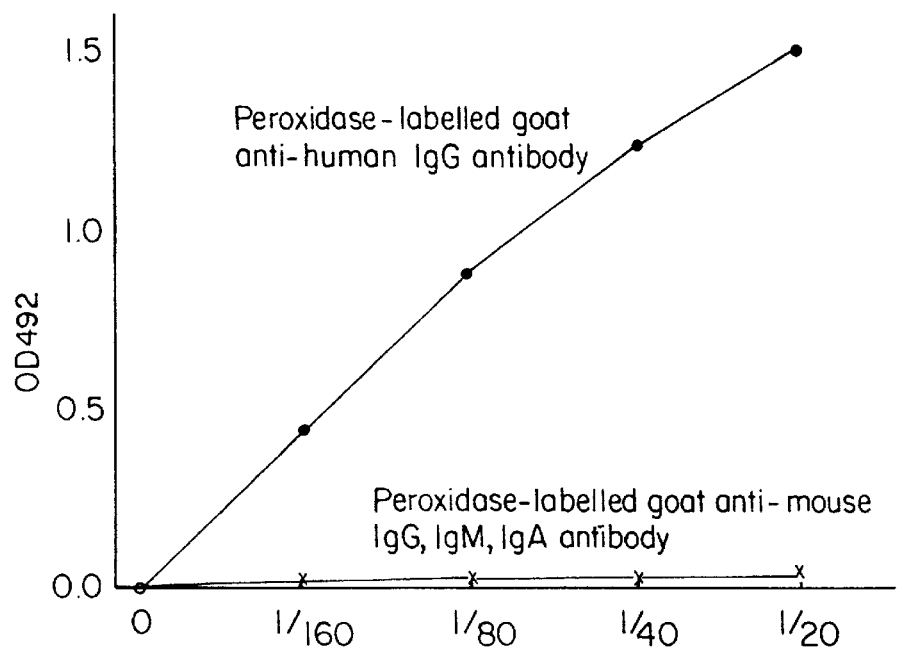
FIG. 1 shows the titer of an anti-KLH IgG antibody in the serum of immunodeficient mice which received human peripheral lymphocytes.

The immunodeficient animals which may be employed in the method of the present invention are those which do not exhibit rejection when human lymphocytes are transplanted to the animals. Such animals may be artificially prepared by physical, chemical or biological treatments. Any immunodeficient animal may be employed. C.B-17/Icr-scid mice (G. C. Bosma et al., Nature, 301, 527 (1893)) are particularly preferred because of their commercial availability.

The human lymphocytes may be obtained from human peripheral blood, spleen, lymph nodes, tonsils or the like.

The taking of the transplanted human lymphocytes in the animals can be attained by merely administering the human lymphocytes to the animals. The administration route is not restricted and may be subcutaneous, intravenous or intraperitoneal. The dose of the human lymphocytes is not restricted, and can usually be $10^6$ to $10^8$ lymphocytes per animal.

The immunodeficient animal is then immunized with a desired antigen. The method of immunization per se is well-known in the field of monoclonal antibodies. For example, the immunization may be carried out by the method described in Sakuji TOYAMA et al., ed. "Monoclonal Antibody, Experiment Manual", published by Kodansha Scientific (1987).

After the immunization, human lymphocytes are recovered from the blood, spleen, lymph nodes or other lymphatic tissues. This may be achieved by a conventional method. For example, firstly, mononuclear cells are separated by the Ficoll-Hypaque (specific gravity: 1.077) centrifugation method and then monocytes are removed by the plastic dish adsorption method. The contaminating cells originating from the animal may be removed by using an antiserum specific to the animal cells. The antiserum may be obtained by, for example, immunizing the animal with the spleen cells of the animal and recovering serum from the immunized animal. The treatment with the antiserum may be carried out at any stage. The human lymphocytes may also be recovered by an immunological method employing a human immunoglobulin expressing on the cell surface as a marker. By these methods, human lymphocytes mainly producing IgG and IgA antibodies specific to the desired antigen can be obtained.

Monoclonal antibodies may be obtained from the thus obtained human lymphocytes producing the desired antibodies by the following method: First, the human lymphocytes are immortalized. The methods of immortalizing lymphocytes are well-known in the art. For example, the immortalization may be achieved by the transformation method using Epstein-Barr virus (EBV) (D. Kozbor et al., supra). Alternatively, the cell fusion method widely employed for the production of monoclonal antibodies (T. Kudo et al., Tohoku J. Exp. Med. 154, 345 (1988)) may be-employed. The combination of these methods may also be employed. In an especially preferred embodiment, the above-mentioned transformation method and the cell fusion method are combined. More particularly, for example, the lymphocytes obtained by the above-described method are washed with phosphate buffer and then infected with EBV. The reactivities of the antibodies in the culture supernatants are then checked by ELISA employing HD antigen, and the lymphocytes which exhibit high reactivity are grown. The resulting lymphocytes are then fused with a parent line of human or mouse origin. As the parent line, known myeloma cells may be employed. Examples of the parent line of human origin include KR-12 (J. Immunol. 133, 3001 (1984)) and W1L-2NS (ATCC CRL8/55, Cancer 22:517–524 (1968)). Examples of the parent line of mouse origin include SP2/0 (ATCC CRL8006, J. Virol. 36:547–555 (1980)), P3×63 (ATCC CRL1580, J. Immunol. 123:1548–1550 (1979)) and NS-1 (ATCC T1B18, Eur. J. Immunol. 6:511 (1976)). Examples of human/mouse hybrid parent line include SHM-D33 (ATCC CRL1668)). Still alternatively, the immunodeficient animal may be directly infected with EBV after the above-described immunization and the transformed human lymphocytes may be recovered from the animal. It is intended that this mode is also within the scope of the present invention.

The recovery of the monoclonal antibody from the thus prepared immortalized cells may be achieved by the method widely employed in the production of monoclonal antibodies. That is, the desired monoclonal antibody may be obtained by cloning the immortalized lymphocyte by the limiting dilution method or the like, selecting the cell producing the desired antibody, growing the selected cells in a medium or the abdominal cavity of an animal, and recovering the desired monoclonal antibody from the culture supernatant or ascites.

By the above-described method of the present invention, a human monoclonal antibody which specifically reacts with Hanganutziu-Deicher antigen (HD antigen) was first provided. HD antigen is a glycolipid which exists in tissues and sera of animals but which does not exist in normal tissues and normal sera of humans and chickens. However, even in humans, HD antigen is observed on the surfaces of cancer cells and in sera of cancer patients. HD antigen includes HD3, HD5 and HD7 antigens, mentioned in the order of mobilities in thin layer chromatography (TLC). In the interim, HD3 antigen specifically exists in liver cancer, melanoma, retinoblastoma and the like. Thus, if a monoclonal antibody which specifically reacts with HD antigen exists, it is expected that the monoclonal antibody may be used for the diagnosis and therapy of cancers.

However, since HD antigen exists in animals other than humans and chickens, the ordinary method for producing monoclonal antibodies which employs an animal such as a mouse cannot be applied to the production of a monoclonal antibody specific to HD antigen.

A monoclonal antibody derived from chickens, which specifically reacts with HD antigen is known (Ohashi et al., Hanganutziu-Deicher heterophile antigen in human retinoblastoma cells, Am. J. Ophthamol., 96:321). Further, production of an anti-HD human monoclonal antibody by in vitro sensitization is also known (Japanese Laid-open Patent Application No. 202295/89). However, these monoclonal antibodies have the above-mentioned drawbacks.

By virtue of the present invention by which the drawbacks of these known methods are overcome, a human monoclonal antibody which specifically reacts with Hanganutziu-Deicher antigen (HD antigen) was first provided. In an especially preferred mode, 10–500 $\mu$g of HD antigen is mixed with an equivolume of adjuvant and the mixture is intraperitoneally administered to a mouse every 2–3 weeks. Further, 10–500 μg of HD antigen is suspended in physiological saline and the suspension is intraperitoneally or intravenously administered. The HD antigen may easily be obtained. For example, the HD3 antigen isolated from horse red blood cells and HD5 antigen and HD7 antigens isolated from bovine red blood cells by the method described in Higashi et al., Biochem. Biophys. Res. Commun., 79, 388 (1977) may be used. The details are described in Example 4 hereinbelow.

Further, by the method of the present invention, a monoclonal antibody specific to the extracellular domain of the human c-erbB2 cancer gene product was obtained. The details are described in Example 3 hereinbelow. This monoclonal antibody may be used in the diagnosis and therapy of cancers, especially stomach cancer.

It should be noted that the claims directed to a monoclonal antibody of the present invention, such as monoclonal IgG antibody, encompass equivalents of the monoclonal antibody such as fragments having the immunological specificity, monoclonal antibodies labelled with a marker which gives a detectable signal and fragments thereof, and monoclonal antibodies labelled with a toxin and fragments thereof. These equivalents of the monoclonal antibody may easily be prepared by known methods.

The present invention will now be described by way of examples thereof. It should be noted that the examples are presented for illustration purposes only and should not be interpreted in any restrictive way.

Example 1
Human Monoclonal Antibody Specific to KLH (Keyhole Lympet Hemocyanin)
(1) Transplantation of Lymphocytes and Immunization of Animals Human peripheral lymphocytes were transplanted to 6 week old C.B-17/Icr-scid mice (female) (commercially available from CLEA Co., Ltd.) in an amount of $4 \times 10^7$ cells/mouse. The separation of peripheral lymphocytes was carried out by the Ficoll-Hypaque (specific gravity: 1.077) centrifugation method. Then 0.1 mg of KLH was dissolved in 0.2 ml of Dulbecco's phosphate buffered saline (PBS) and the resultant was emulsified with the same volume of Freund's complete adjuvant. The obtained emulsion was intraperitoneally administered to each mouse.

For the subsequent immunization, Freund's incomplete adjuvant was used, and immunization was carried out six times over two months. The profile of increasing human IgG specific to KLH in the sera of the immunized animals is shown in FIG. 1. The data shown in FIG. 1 were obtained by an ELISA ($OD_{492}$) carried out by adding the immunized mouse serum to wells of a microplate coated with KLH, and after reaction and washing with water, adding a second antibody that was peroxidase-labelled goat anti-human IgG or anti-mouse IgG, IgM or IgA.

Figure 2:
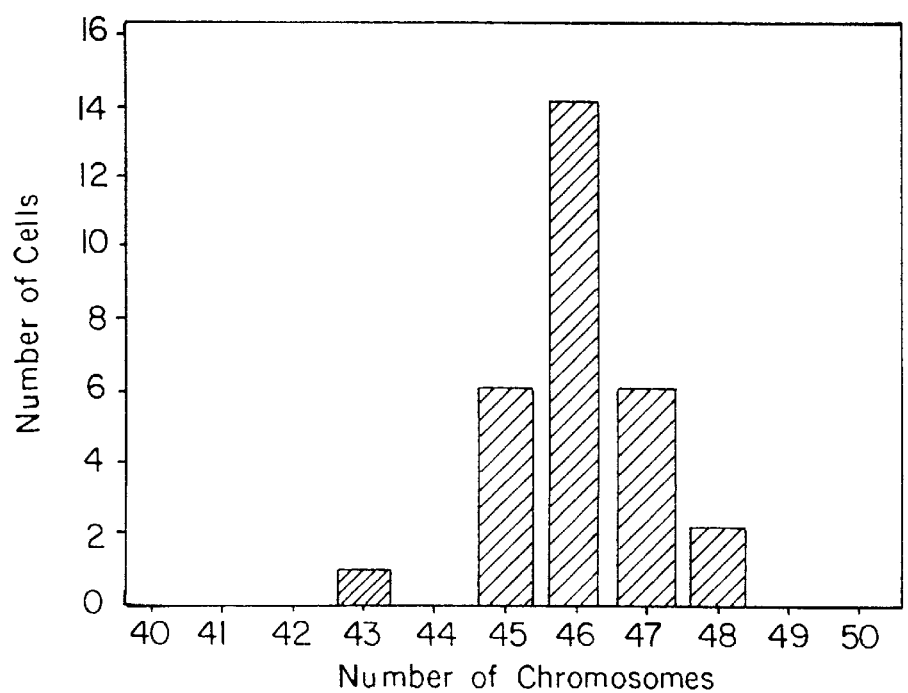
FIG. 2 shows the distribution of the number of chromosomes in the cells prepared by transforming the antibody-producing lymphocytes with EBV.

(2) Recovery of Human Lymphocytes from Immunized Mice and Transformation Thereof After the immunization, a preliminarily prepared antiserum was intraperitoneally administered to the mice and the spleens of the mice were removed 9 hours after the administration of the antiserum. The antiserum was obtained by intravenously administering C.B-17/Icr-scid mouse spleen cells into a rabbit (Japanese white species) as an antigen four times every two weeks, recovering the blood after the immunization, separating serum, and subjecting the serum to salting out with 33% sodium ammonium. The spleen cells were dispersed (Sakuji TOYAMA et al., ed., supra), and human lymphocytes were recovered by the Ficoll-Hypaque (specific gravity: 1.077) centrifugation method. The obtained lymphocytes were subjected to transformation with EBV (T. Kudo et al., supra) to obtain transformed cells (B lymphoblast-like cells). The numbers of chromosomes of the thus obtained cells were determined. As a result, as shown in FIG. 2, it was proved that the cells were of human origin.

Figure 3A:
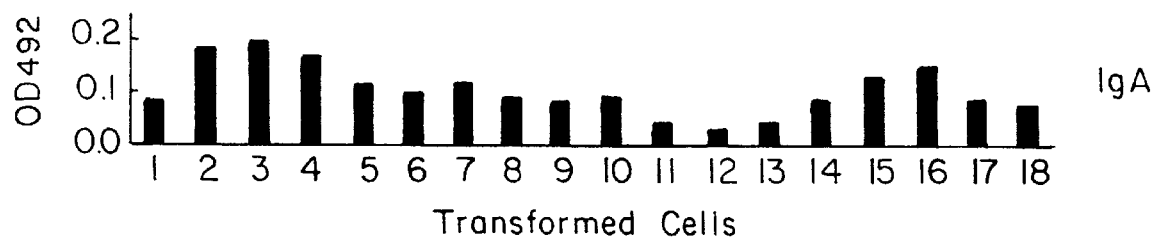
FIG. 3 shows the results of the determination of the anti-KLH antibody in the cell supernatants of transformed cells.
Figure 3B:
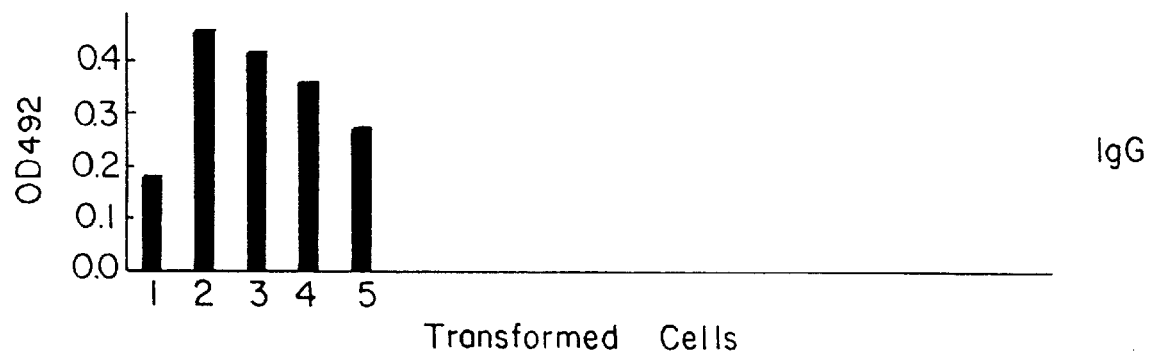
Figure 3C:
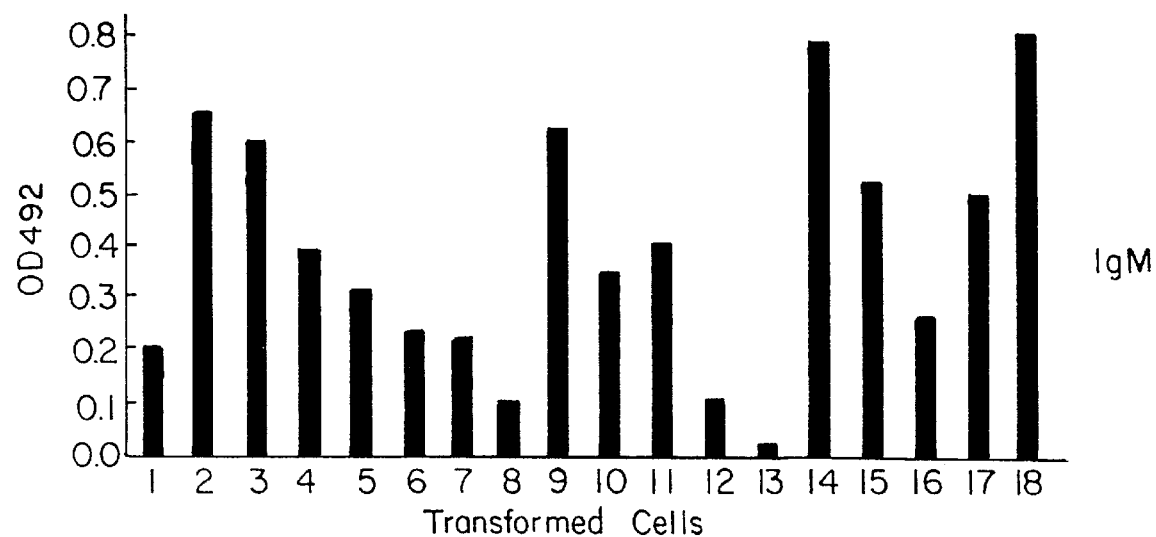

Among the thus obtained transformed cells, 18 cells were tested for the existence of an anti-KLH antibody in the culture supernatant. Into the wells of a microplate coated with KLH, each culture supernatant was added. After allowing the reaction, the wells were washed with water. A second antibody which was anti-human IgA, IgG or IgM goat antibody labelled with peroxidase was added to each well and ELISA was carried out in the conventional way. As a result, as shown in FIG. 3, it was proved that all of the 18 transformed cells produced antibodies specific to KLH.

Figure 4:
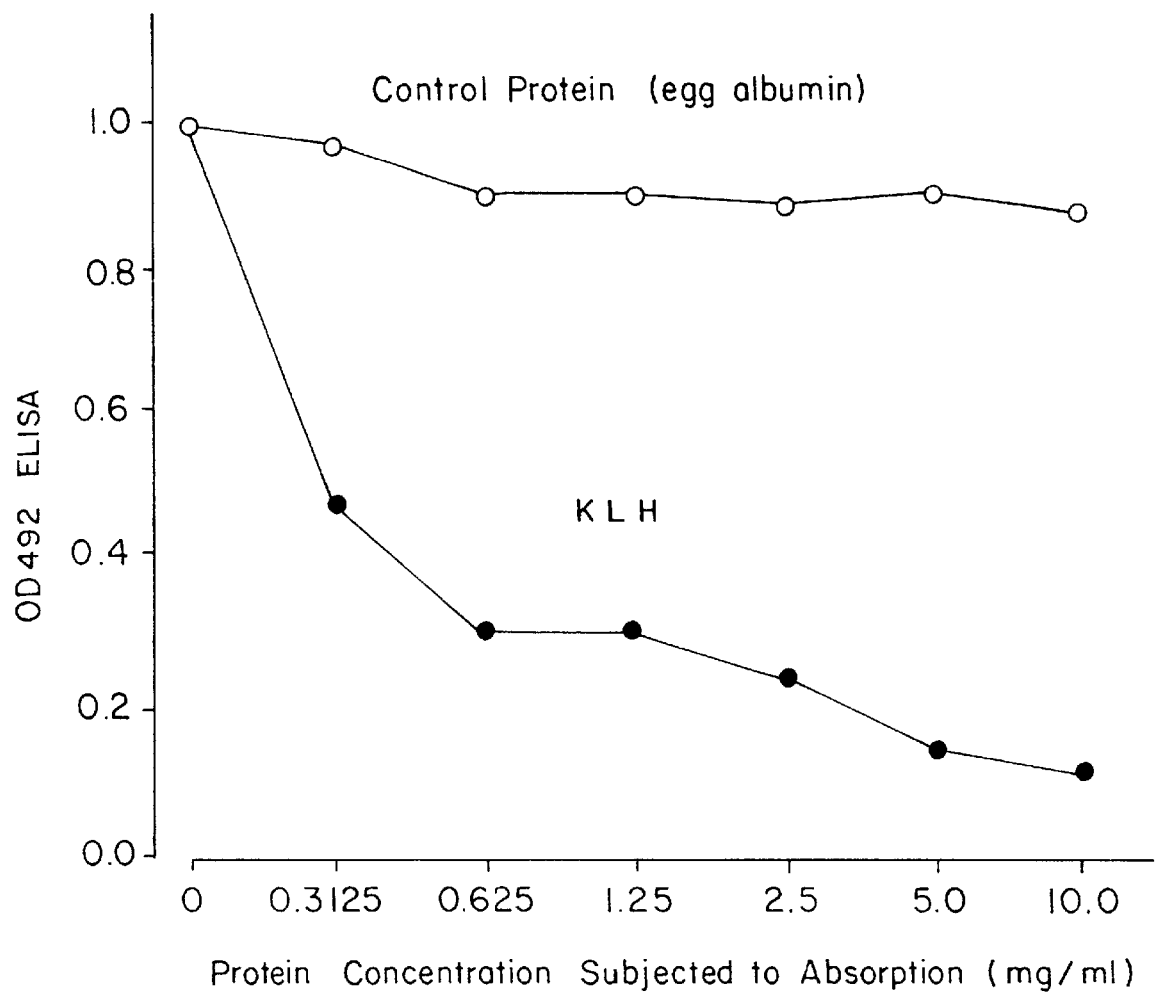
FIG. 4 shows the results of the absorption test between the culture supernatant of a transformed cell (LCL8-9) and KLH.

To assure that the transformed cells produce antibodies specific to KLH, the culture supernatant of one of the transformed cell lines (LCL8–9) was subjected to absorption reaction with KLH. As shown in FIG. 4, it was proved that the produced antibody was specific to KLH.

(3) Cell Fusion of the Transformed Cells and Production of Monoclonal Antibodies The transformed cells were fused with a parent line (mouse×human heteromyeloma cell SHM-D33) (ATCC CRL-1668) by the method of Kudo et al., supra, to establish 13 hybridomas producing anti-KLH antibody.

The classes of the antibodies produced by these hybridomas were determined. The results are shown in Table 1. As shown in Table 1, among the 13 hybridomas, eight produced IgA antibodies, four produced IgG antibodies and one produced IgM antibody.

TABLE 1

Properties of 13 Hybridomas Producing Anti-KLH Antibodies

| No. of Hybridoma | Class of Antibody Produced |
| --- | --- |
| #31 | IgA |
| #64 | IgA |
| #73 | IgA |
| #80 | IgA |
| #84 | IgA |
| #89 | IgA |
| #101 | IgA |
| #149 | IgA |
| #87 | IgG |
| #179 | IgG |
| #191 | IgG |
| #195 | IgG |
| #22 | IgM |

Example 2
Monoclonal Antibodies Specific to AFP (α-fetoprotein)
(1) Transplantation of Lymphocytes and Immunization of Animals To 6 weeks old C.B-17/Icr-scid mice (female) of human peripheral lymphocytes were intraperitoneally administered in an amount of $5 \times 10^7$ cells/mouse. The peripheral lymphocytes were obtained by the Ficoll-Hypaque (specific gravity: 1.077) centrifugation method. Then 0.1 mg of AFP was dissolved in 0.2 ml of Dulbecco's phosphate buffered saline (PBS) and the resultant was emulsified with the same volume of Freund's incomplete adjuvant. The obtained emulsion was intraperitoneally administered to each mouse. One week later and 3 weeks later, the second and the third immunizations were carried out, respectively, in the same manner as in the first immunization.

(2) Transformation by EBV

One week after the third immunization, 1 ml of B95-8 (ATCC CRL1612) culture supernatant was intraperitoneally administered to each mouse. Three weeks later, the mice were sacrificed and peripheral blood, spleen, thymus and mesentery lymphocytes and the like were removed from each mouse. The obtained cells were dispersed in 10% fetal calf serum-containing RPMI1640 medium and the cells were cultured under an atmosphere of 95% air/5% $CO_2$ at 37° C. The grown cells were subcultured and cloned, and then transformed cells were prepared therefrom. In the culture supernatants of the obtained transformed cells, anti-AFP antibodies (human IgG, IgA and IgM) were observed.

Example 3

Human Monoclonal Antibodies Specific to c-erbB2 Cancer Gene Product (1) Preparation of Antigen The N-terminal region of the extracellular domain of human c-erbB2 cancer gene product (amino acid Nos. 495–509), having the amino acid sequence His Thr Ala Asn Arg Pro Glu Asp Glu Cys Val Gly Glu Gly Leu (SEQ ID NO.1) was synthesized and purified by C18-reverse phase HPLC. The obtained synthetic peptide was conjugated with KLH by using a hapten-conjugation kit (commercially available from PIERCE) to prepare an antigen.

(2) Transplantation of Lymphocytes and Immunization of Animals

Human peripheral lymphocytes were intraperitoneally administered to 8 week of C.B-17/Icr-scid mice (female) in an amount of $5 \times 10^7$ cells/mouse. Simultaneously, 60 μg of the antigen were intraperitoneally administered and 50 μg of the antigen were subcutaneously administered to each mouse. Additional immunizations were performed intraperitoneally every week three times.

(3) Cell Fusion and Preparation of Monoclonal Antibodies

Three days after the final immunization, spleens were removed and the blood was hemolyzed by treatment with a hemolyzing agent (Tris-HCl buffer containing 0.125% ammonium chloride). After washing the cells well with RPMI-1640 medium, the cells were fused with mouse× human heteromyeloma cells SHM-D33 (ATCC CRL-1668) by the conventional method. The screening of the fused cells was performed by ELISA using the above-mentioned synthetic peptide conjugated to ovalbumin, and hybridomas producing human monoclonal antibodies specific to c-erbB2 were established. Among these, the human monoclonal antibody produced by hybridoma TKG41 (FERM BP-4055) belongs to IgM and it was confirmed by the cell ELISA method that this monoclonal antibody reacts with the cell membrane of stomach cancer-derived cell Kato III.

Example 4

From 10 ml of human peripheral blood, $10^7$ lymphocytes were separated. The lymphocytes were intraperitoneally transplanted to 5 weeks old SCID mice (female) (FOX CHASE SCID C,B-17/Icr-scid Jcl, (commercially available from KLEA Co., Ltd.)). One hundred micrograms of HD3 antigen (prepared from horse red blood cells by the method of Higashi et al (supra) were mixed with 0.5 ml of Freund's incomplete adjuvant (commercially available from Gibco), and the mixture was intraperitoneally administered. Two weeks later, the same immunization was repeated. After an additional two weeks, a suspension containing 50 μg of HD3 antigen in 1 ml of physiological saline was intraperitoneally administered. Three days later, the mouse was sacrificed and mesentery lymphocytes were recovered. The obtained lymphocytes were washed three times with phosphate buffered saline, and subjected to transformation by EBV by the method of Kudo et al., (supra). The culture supernatants of the transformants were analyzed for the existence of anti-HD3 antibody by using the HD3 antigen to obtain 6 hybridomas producing anti-HD3 antibodies. The transformant SHHD (FERM BP-4053) producing the antibody having the highest reactivity was fused with a SHM-D33 mouse× human heteromyeloma cell line (ATCC CRL 1668). The obtained hybridomas were screened for anti-HD3 antibody using the HD3 antigen, and the hybridoma exhibiting the highest reactivity was cloned by the limiting dilution method to obtain SHHD1 (FERM BP-4054), deposited on Oct. 11, 1992, under the terms of the Budapest Treaty at the Fermentation Research Institute Agency of Industrial Science and Technology, 1–3, Higashi 1 chome Tsukuba-shi Ibaraki-ken 305, JAPAN. It should be noted that a hybridoma producing anti-HD human monoclonal IgG antibody may be derived from the hybridoma SHHD1 by the conventional cell fusion technique.

The reactivity of the monoclonal antibody produced in the culture supernatant of SHHD1 to HD3 antigen was examined by ELISA. That is, 100 μl of HD3 antigen (1 μg/ml) were placed in each well in a microtiter plate and the antigen was immobilized. The non-specific binding sites were blocked with 1% defatted ovalbumin solution in PBS and the wells were washed with 0.05% Tween 20 (trademark). Then 50 μl of the culture supernatant of SHHD1 or dilutions thereof diluted with PBS were added to each well and the wells were washed in the same manner as mentioned above. Then anti-human IgG labelled with peroxidase was added to the wells and the wells were washed in the same manner as mentioned above.. Thereafter, o-phenylenediamine and sulfuric acid were added to color the mixture and the absorbance at 492 nm was measured. As a control, the same experiment was carried out except that standard IgG was used in place of the culture supernatant. The results are shown in FIG. 5.

Figure 5:
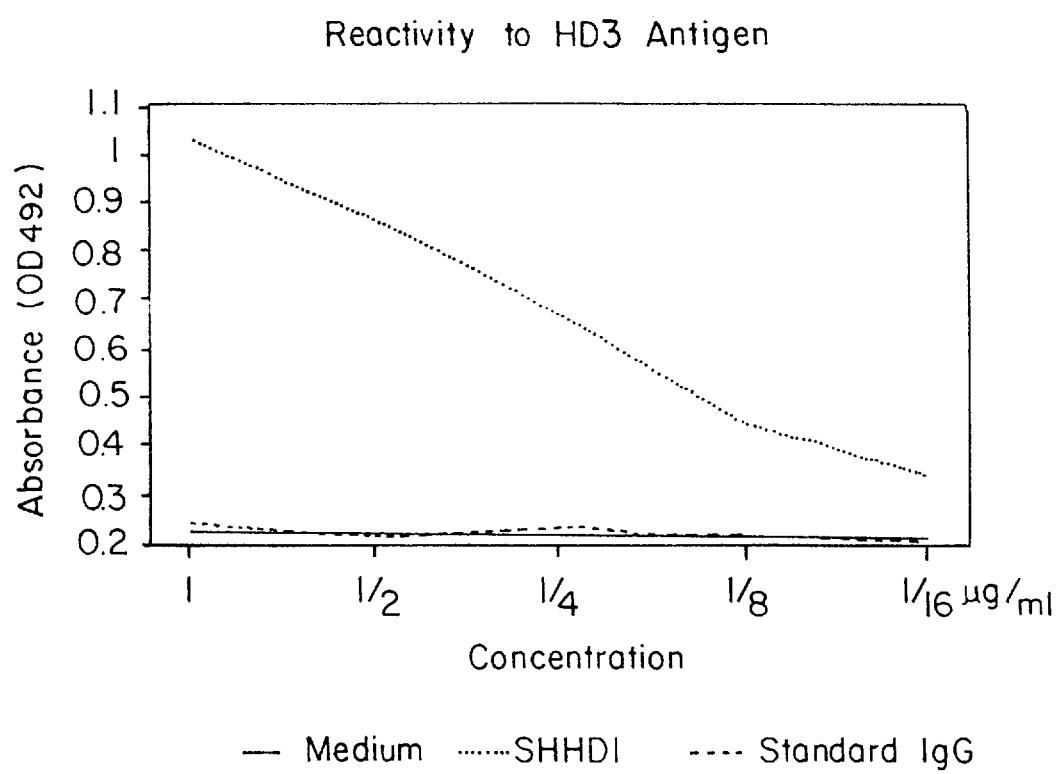
FIG. 5 shows the results of ELISA for determining the reactivity of a monoclonal antibody produced in the culture supernatant of SHHD1 to HD3 antigen.

As shown in FIG. 5, the reactivity of the culture supernatant of SHHD1 varies depending on its concentration. Thus, it was proved that an anti-HD3 monoclonal antibody existed in the culture supernatant.

It was determined that this monoclonal antibody belongs to IgG by the Ouchterlony method.

Figure 6A:
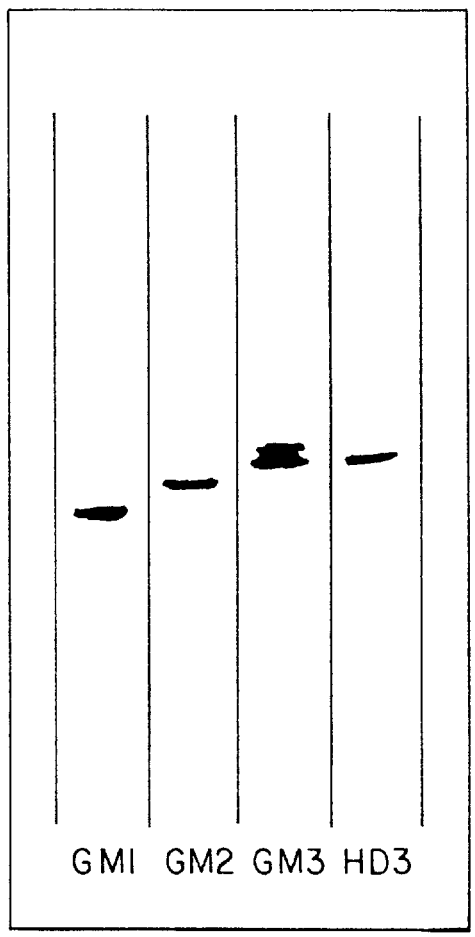
FIGS. 6A and 6B show the results of the TLC immunostaining for determining the reactivities of the SHHD1 monoclonal antibody with various ganglioside.
Figure 6B:
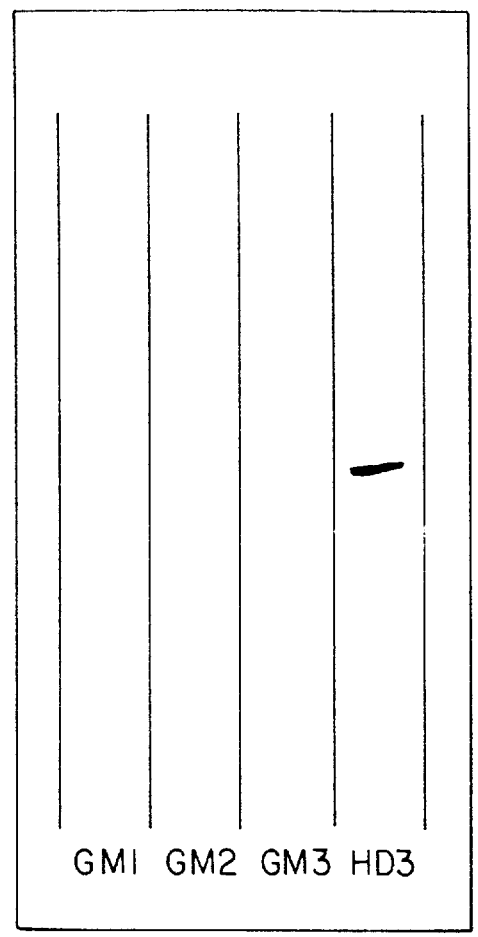

The reactivity of purified monoclonal antibody SHHD1 labelled with an enzyme was examined by the TLC-immunostaining method. That is, 3 μg each of GM1, GM2, GM3 and HD3 antigen were developed in a HPTLC plate (commercially available from Merck) and the plate was treated with polyisobutylmethacrylate. A diluted solution prepared by diluting 100 μg/ml of the enzyme-labelled SHHD1 with 1% chicken serum was reacted with the plate for one hour and the resultant was colored by adding diaminobentidine to the plate. The results are shown in FIG. 6b. The results obtained by coloring the plate with orcinol sulfate are shown in FIG. 6a.

As is apparent from FIG. 6, the monoclonal antibody SHHD1 specifically reacts with HD3 antigen.

Anti-HD polyclonal antibody (10 μg/ml) obtained from a chicken was placed in the wells of a microtiter plate to immobilize the antibody. The non-specific binding sites in the wells were blocked with 1% ovalbumin (defatted by ultracentrifugation) in PBS, and the wells were washed with 0.05% Tween 20 (trademark) in PBS. Then HD3 antigen serially diluted with PBS, normal human serum or serum from a melanoma patient diluted with PBS was placed in the wells in an amount of 50 μl/well. Then peroxidase-labelled SHHD1 monoclonal antibody was added to each well and the wells were washed as mentioned above. The mixture in each well was colored by adding thereto o-phenylenediamine solution and sulfuric acid and the absorbance at 492 nm of the resultant was measured. As a control, the same experiment was carried out except that PBS was used in place of HD3 antigen. The results are shown in FIG. 7 and in Table 2.

TABLE 2

| | HD Antigen Level in Blood |
|---|---|
| Normal Serum | 0 |
| Melanoma Serum | 100 μg/ml |

Figure 7:
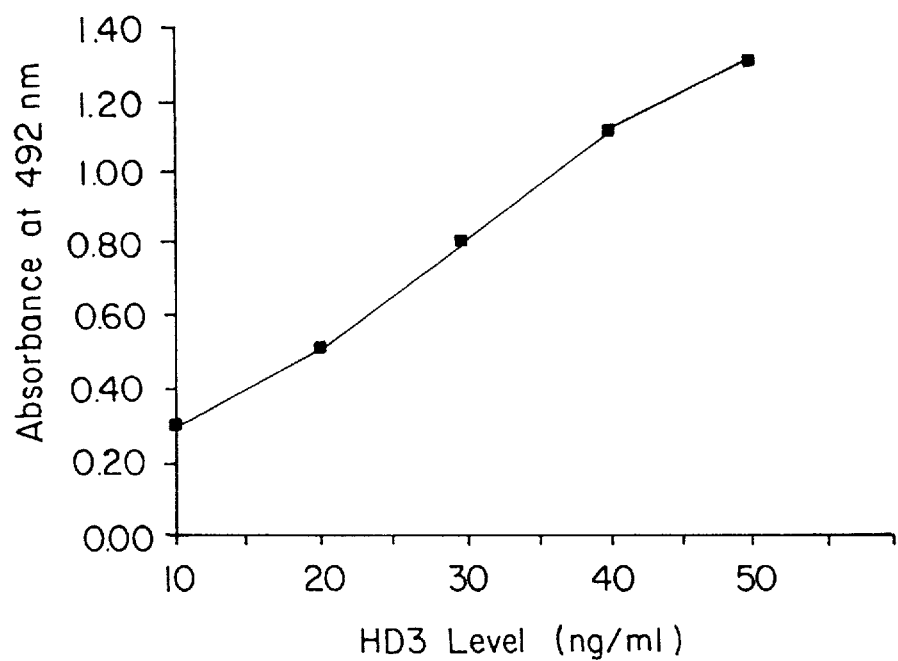
FIG. 7 shows a calibration curve for assay of HD antigen, which was prepared by using SHHD1 monoclonal antibody.

As is apparent from FIG. 7 and Table 2, by using this antibody, the HD antigen level in blood can be determined and it was observed that the HD antigen level in blood of the melanoma patient is significantly higher than in blood of normal humans. This indicates that diagnosis of cancer cells can be achieved by using this antibody.

Agglutinated horse pancreas and human melanoma sections were thinly sliced and attached to glass slides, followed by fixation with 4% paraformaldehyde. The samples were treated with 0.3% hydrogen peroxide to inhibit the endogenous peroxidase activities. Then peroxidase-labelled SHHD1 antibody diluted with 1% chicken serum was added to the samples. After allowing the reaction, the samples were sufficiently washed with PBS and then diaminobentidine solution was added to color the samples. As a control, the same experiment was repeated except that peroxidase-labelled human IgG was used in place of the peroxidase-labelled SHHD1 antibody. The results are shown in Table 3.

TABLE 3

| | SHHD1 | Standard IgG |
|---|---|---|
| Horse Pancreas | ++ | -- |
| Melanoma | ++ | -- |

As is apparent from Table 3, the existence of HD antigen in a tissue can be immunohistochemically detected. Further, it was proved that HD antigen expresses on the melanoma section from a melanoma patient.

To nude mice transplanted with melanoma cells, standard IgG, SHHD1 monoclonal antibody or ricin-conjugated SHHD1 monoclonal antibody was administered in an amount of 1 mg/mouse. The mean tumor volumes were measured every 5 days. The tumor volumes were calculated from the formula $d_1 \times d_2 \times d_3 \times \pi/2$. The results are shown in FIG. 8.

Figure 8:
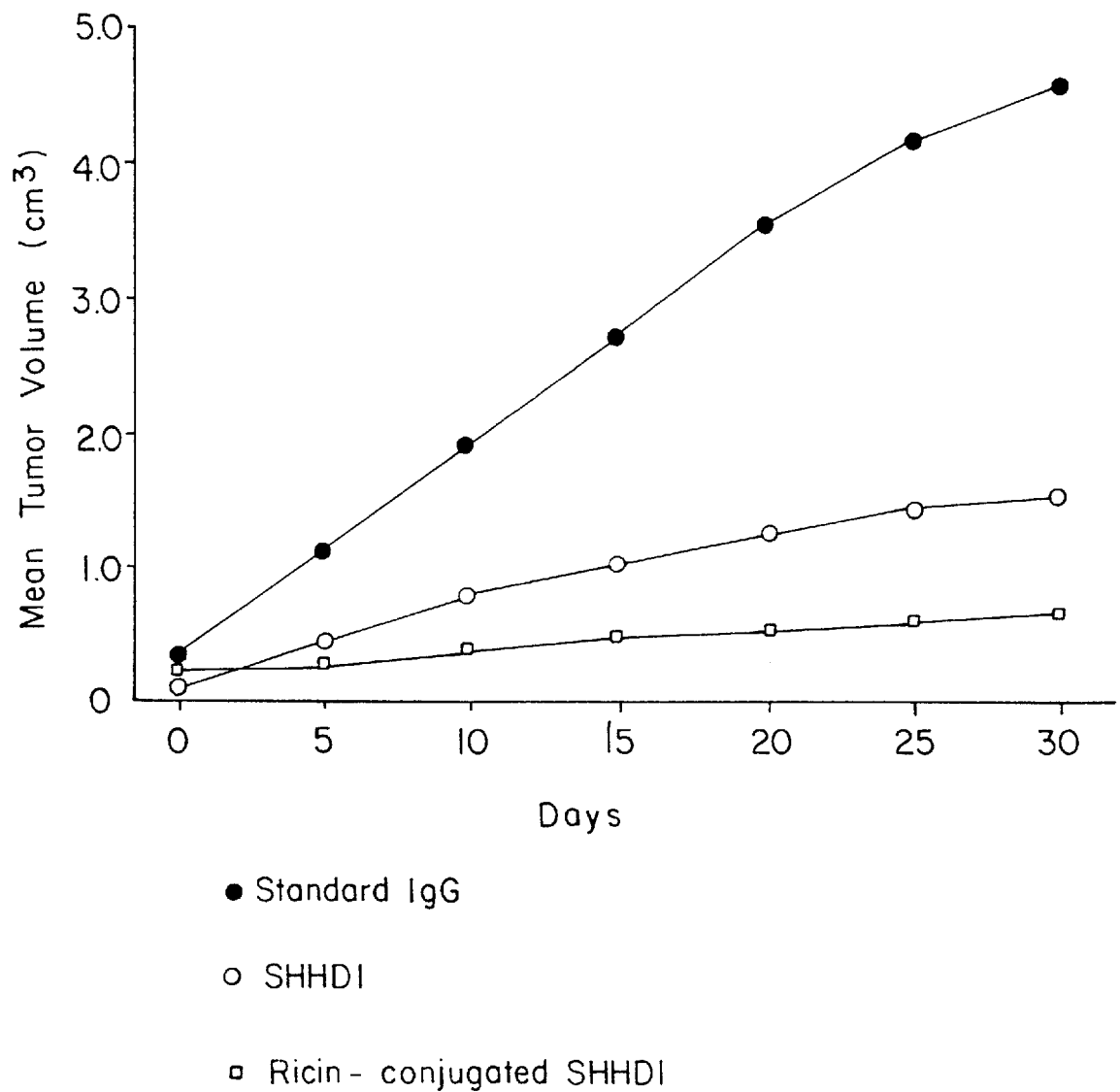
FIG. 8 shows the mean tumor volumes of nude mice which received various antibodies.

As shown in FIG. 8, SHHD1 monoclonal antibody and ricin-conjugated SHHD1 monoclonal antibody exhibited anti-tumor effects. Thus, it was proved that immunotherapy against cancer cells can be carried out by administering the anti-HD monoclonal antibody.

Although the present invention is described by way of preferred embodiments thereof, it is apparent for those skilled in the art that various modifications may be made within the spirit and scope of the present invention.

We claim:

1. An anti-HD human monoclonal IgG antibody which specifically reacts with HD antigen.

2. The monoclonal antibody of claim 1, wherein said HD antigen is HD3 antigen.

3. A cell line which produces said monoclonal antibody of claim 1.

4. The cell line of claim 3, which is SHHD1 (FERM BP-4054).

5. A method for screening for the presence of cancer cells comprising, in the order mentioned, the steps of:

mixing the monoclonal antibody of claim 1 with a sample; and detecting binding of said monoclonal antibody with HD antigen, wherein said binding indicates the presence of cancer cells.

6. The method of claim 5, wherein said HD antigen is HD3 antigen.

7. A cell line producing said monoclonal antibody of claim 1, which cell line is derived from SHHD1.

8. The anti-HD human monoclonal IgG antibody of claim 1, wherein said antibody is a member selected from the group consisting of said antibody per se, a fragment of said antibody having the immunological specificity thereof, a monoclonal antibody labelled with a marker which produces a detectable signal, and a fragment thereof, a monoclonal antibody labelled with a toxin and a fragment thereof.

9. A method of treating cancer with immunotherapy comprising administering to a patient in need thereof a human monoclonal IgG antibody of claim 1.

10. A method for screening for the presence of cancer cells comprising, in the order mentioned, the steps of:

mixing the monoclonal antibody of claim 1 with a sample; and detecting binding of said monoclonal antibody with HD antigen by using an ELISA assay, wherein said binding indicates the presence of cancer cells.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:1:

His Thr Ala Asn Arg Pro Glu Asp Glu Cys Val Gly Glu Gly Leu
    1                  5                  10                 15